United States Patent
Mamana

(10) Patent No.: US 7,211,604 B2
(45) Date of Patent: *May 1, 2007

(54) COMPOUNDS FOR BLOCKING ANDROGEN RECEPTORS

(75) Inventor: John P. Mamana, McLean, VA (US)

(73) Assignee: Trident Sciences LLC, Vienna, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/888,544

(22) Filed: Jul. 12, 2004

(65) Prior Publication Data

US 2004/0266884 A1 Dec. 30, 2004

Related U.S. Application Data

(63) Continuation of application No. 10/338,889, filed on Jan. 9, 2003, now Pat. No. 6,768,026.

(60) Provisional application No. 60/346,545, filed on Jan. 9, 2002.

(51) Int. Cl.
*A61K 31/12* (2006.01)
*C07C 49/105* (2006.01)

(52) U.S. Cl. ................................. 514/690; 568/377

(58) Field of Classification Search ............... 568/377; 514/690
See application file for complete search history.

(56) References Cited

U.S. PATENT DOCUMENTS 6,768,026 B2 * 7/2004 Mamana .................... 568/377

* cited by examiner

*Primary Examiner*—Sikarl A. Witherspoon
(74) *Attorney, Agent, or Firm*—McGuireWoods LLP

(57) ABSTRACT

Compounds used to block non-essential androgen receptors are described. In particular, cyclohexenone compounds containing an alkyl group may be used in the treatment of conditions mediated by the blocking of non-essential androgen receptors such as acne, male patterned baldness, keloids, skin-wrinkling, and osteoarthritis. The cyclohexenone compound may be administered orally, topically, or internally.

8 Claims, No Drawings

COMPOUNDS FOR BLOCKING ANDROGEN RECEPTORS

RELATED APPLICATIONS

This application is a continuation of U.S. application Ser. No. 10/338,889, filed on Jan. 9, 2003, now U.S. Pat. No. 6,768,026 which claims priority to and is related to U.S. Provisional Application No. 60/346,545, filed Jan. 9, 2002, each application herein incorporated by reference in their entirety.

FIELD OF THE INVENTION

The present invention is directed to compounds that are useful for treating conditions mediated by blocking non-essential androgen receptors in a patient.

BACKGROUND OF THE INVENTION

It is well know that androgen plays a significant role in causing a variety of conditions such as acne and male patterned baldness. Other conditions that are thought to be related to androgen include keloids, adhesions, elastin synthesis, wrinkling effects, and osteoarthritis.

Methods for treating conditions mediated by or related to androgen include blocking the associated androgen receptors. There are different types of androgen receptors and they may be broadly separated into two basic groups, essential androgen receptors and non-essential receptors. Generally, compounds that are effective in blocking androgen receptors are referred to as anti-androgen compounds or androgen blockers.

Compounds that block the non-essential receptors are of particular importance because these compounds tend to be effective at treating conditions mediated by androgen without causing anti-androgen-like responses, such as affecting sexual potency or libido.

SUMMARY OF THE INVENTION

The present invention is directed to cyclohexenone compounds that may used to block androgen receptors in a patient. The compounds are stable at room temperature and may be used in various compositions for topical application, oral, or internal administration.

DETAILED DESCRIPTION OF THE INVENTION

Some compounds used to block androgen receptor sites have utilized cyclic and bicyclic alkanone rings with a pendent alkyl moiety. In some of these compounds, alkyl moiety and the cyclic ring is separated by a carbon-carbon double bond. Typically, these compounds are difficult to prepare and are unstable at room temperature and when exposed to light. These properties make them undesirable candidates for commercial compositions and treatment methods.

In contrast compounds of the present invention are stable under ambient conditions and may be stored at room temperature and are stable in the presence of light. Compounds of the present invention may be referred to generally as cyclohexenone compounds. Of particular importance are 3-(5-methoxyheptyl)-2-cyclohexenone and 3-(5-ethoxyheptyl)-2-cyclohexenone. These compounds contain a cyclohexenone group with an alkyl moiety as shown generally in Structure 1.

Structure 1.

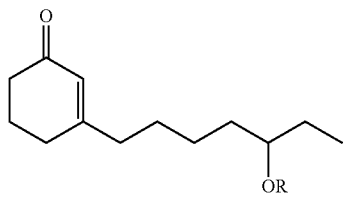

The alkyl moiety on the cyclohexenone group has an alkoxy moiety represented by OR where R is an alkyl group. In a preferred embodiment, R is methyl or ethyl.

The chemical terms and names in the present description refer to and cover compounds falling within the definition of that term or name as classically used in organic chemistry. The compounds of the present invention may have one or more chiral centers and may exist in enantiomeric and diastereomeric forms. The scope of the present invention is intended to include all such forms of the compound.

The compounds of the present invention may be prepared by known methods following general organic chemistry synthesis procedures and pathways known to those skilled in the art. Generally the alkyl group may be prepared separately and then combined with a cyclic reagent to produce the cyclohexenone compound as illustrated in Scheme 1 below. The compounds may also be prepared from nutraceutical starting materials such as biotin and β-carotene.

Scheme 1.

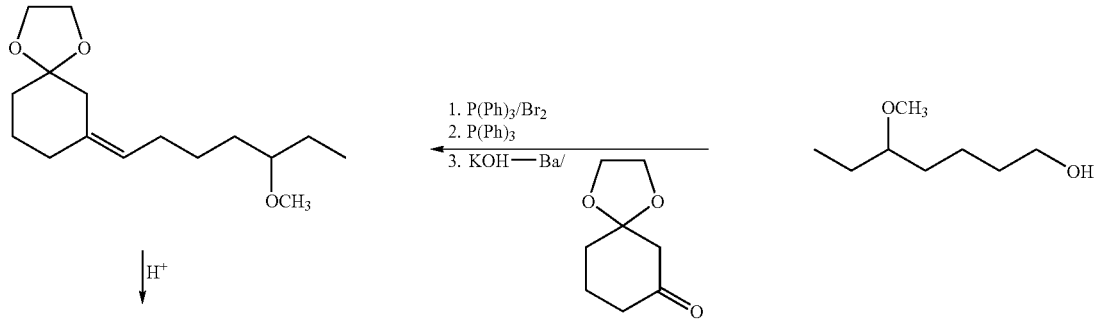

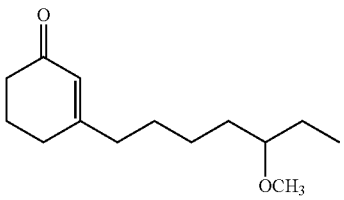

The compounds of the present invention have desirable anti-androgen activity in that the compounds are effective for treating conditions mediated by androgen or by blocking androgen receptors. These conditions may include, but are not limited to, acne vulgaris, androgenic alopecia or male patterned baldness, osteoarthritis, inhibiting breast capsule formation around a foreign body mammary insert, keloids, adhesions, and skin wrinkling. Further, the compounds of the present invention are substantially selective by acting primarily on non-essential androgen receptors.

The cyclohexenone compounds of the present invention are stable at room temperature and in the presence of light for extended periods of time. This stability makes them good candidates for use in compositions to treat androgen mediated conditions by blocking androgen receptors.

The compounds of the invention may be administered to block non-essential androgen receptors. Generally, the treatment of any disease or condition mediated by androgen or androgen receptors in mammals will be effected by the administration of a therapeutically effective dose of one or more of the cyclohexenone compounds of the present invention. A therapeutically effective dose is the amount of the compound required to block enough androgen receptors in a patient, either animal or human, to improve the condition. The amount of the compound will vary depending on the type of condition, severity of the condition, and other dependent patient variables known to those skilled in the art. The cyclohexenone compounds may be administered orally, typically, or internally. For most patients it is believed that an oral dose ranging from about 0.0001 mg to about 30 mg will be effective for blocking androgen receptors to improve the condition being treated. Preferably, the oral dose ranges from about 0.01 to about 5 mg. When taken orally the cyclohexenone compounds may be in the form of a tablet, capsule, suspension, solution, or other form suitable for oral delivery.

In a preferred embodiment, a topical composition containing the cyclohexenone compounds of the invention is applied topically to the desired area on the patient. Topical compositions may take the form of ointments, creams, shampoos, solution components for mixing with the compound, and the like. The cyclohexenone compound, when part of a topical composition, is preferably in a concentration of about 0.001% to about 10% by weight, more preferably from about 0.05% to about 5% by weight of the topical composition.

The topical composition may include a variety of additives. Virtually any additive may be used, so long as the additive does not chemically modify the compound or prevent the compound from blocking androgen receptors. Some additives include, but are not limited to, fillers, sun screens, moisturizers, and color components.

The compounds of the present invention may be administered internally by injection or intraveneously. When administered internally or intraveneously, the cyclohexenone compound should be dissolved or suspended in a solution suitable for injection or intravenous administration. Such solutions include, but are not limited to, saline solutions, lactated ringers solution, water, and other similar solutions.

Further, other components that may aid in treating the condition may be combined with the compounds of the present invention. For example, a topical composition for treating acne may include compounds of the present invention combined with benzoyl peroxide, retin A, vitamin E emollient, or a combination of these components. In this way, the condition may be treated by using components that can control other variables related to the condition.

While the invention has been described in terms of its preferred embodiments, those skilled in the art will recognize that the invention can be practiced with modification within the spirit and scope of the appended claims.

What is claimed is:

1. A topical composition comprising:
a compound having the formula:

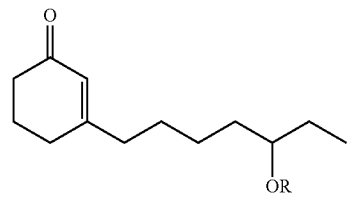

wherein said compound is in a concentration ranging from about 0.001% to about 10% by weight of the topical composition and wherein R is selected from the group consisting of H and alkyl.

2. The compound in accordance with claim 1, wherein R is $CH_3$.

3. The topical composition of claim 1, wherein said concentration ranges from about 0.05% to about 5% by weight of the topical composition.

4. The topical composition of claim 2, wherein said concentration ranges from about 0.05% to about 5% by weight of the topical composition.

5. An oral composition comprising:
a compound having the formula:

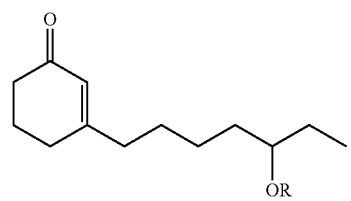

wherein said compound is in an amount ranging from about 0.0001 mg to about 30 mg and wherein R is selected from the group consisting of H and alkyl.

6. The oral composition of claim 5, wherein R is $CH_3$.

7. The oral composition of claim 5, wherein said amount ranges from about 0.01 mg to about 5 mg.

8. The oral composition of claim 6, wherein said amount ranges from about 0.01 mg to about 5 mg.

* * * * *